United States Patent
Lippert et al.

(10) Patent No.: US 12,220,206 B2
(45) Date of Patent: Feb. 11, 2025

(54) IMAGE-CAPTURING DEVICE, SYSTEM AND METHOD FOR CAPTURING IMAGES

(71) Applicants: Leibniz-Institut für Neurobiologie Magdeburg, Magdeburg (DE); Otto-von-Guericke-Universität Magdeburg, Magdeburg (DE)

(72) Inventors: Michael Lippert, Magdeburg (DE); Martin Deckert, Magdeburg (DE); Frank W. Ohl, Osterweddingen (DE); Bertram Schmidt, Villingen-Schwenningen (DE)

(73) Assignees: Otto-von-Guericke-Universität Magdeburg, Magdeburg (DE); Leibniz-Institut für Neurobiologie Magdeburg, Madgeburg (DE)

( * ) Notice: Subject to any disclaimer, the term of this patent is extended or adjusted under 35 U.S.C. 154(b) by 687 days.

(21) Appl. No.: 17/289,561

(22) PCT Filed: Oct. 16, 2019

(86) PCT No.: PCT/EP2019/078095
§ 371 (c)(1),
(2) Date: Apr. 28, 2021

(87) PCT Pub. No.: WO2020/088937
PCT Pub. Date: May 7, 2020

(65) Prior Publication Data
US 2022/0015640 A1     Jan. 20, 2022

(30) Foreign Application Priority Data
Nov. 1, 2018 (DE) .................... 10 2018 127 339.8

(51) Int. Cl.
*A61B 5/00* (2006.01)
*G02B 3/00* (2006.01)
(Continued)

(52) U.S. Cl.
CPC .......... *A61B 5/0082* (2013.01); *A61B 5/0071* (2013.01); *A61B 5/0077* (2013.01);
(Continued)

(58) Field of Classification Search
None
See application file for complete search history.

(56) References Cited

U.S. PATENT DOCUMENTS

2008/0214940 A1 * 9/2008 Benaron ............... A61B 5/418
   600/478
2009/0054791 A1 * 2/2009 Flusberg ............. A61B 5/0059
   600/478
(Continued)

FOREIGN PATENT DOCUMENTS

DE   10 2005 051 035    * 10/2005
JP       2013036991 A    2/2013
(Continued)

OTHER PUBLICATIONS

English translation of DE 10 2005 051 035 (Year: 2007).*
(Continued)

*Primary Examiner* — Katherine L Fernandez
(74) *Attorney, Agent, or Firm* — WCF IP

(57) ABSTRACT

The invention relates to an image-capturing device for the miniaturized near-field image capture of biological tissue, in particular for the imaging of genetic indicators. The image-capturing device comprises at least one digital image sensor and an objective lens in the form of a rod-shaped gradient index lens (GRIN), which objective lens is coupled to the digital image sensor for image capture. The objective lens is connected to the digital image sensor to from a monolithic, fixed assembly. There is no mechanical separating interface between the objective lens and the digital image sensor by means of which the digital image sensor can be separated (Continued)

from the objective lens by the user. The invention further relates to a system for the miniaturized near-field image capture of biological tissue, said system comprising an image-capturing device of this type and an evaluation device connected to the image-capturing device.

9 Claims, 1 Drawing Sheet

(51) Int. Cl.
    *G02B 21/00*      (2006.01)
    *G02B 21/02*      (2006.01)
    *G02B 21/16*      (2006.01)
    *G02B 21/36*      (2006.01)
    *H04N 25/00*      (2023.01)

(52) U.S. Cl.
CPC ....... *G02B 3/0087* (2013.01); *G02B 21/0008* (2013.01); *G02B 21/02* (2013.01); *G02B 21/16* (2013.01); *G02B 21/36* (2013.01); *A61B 5/4064* (2013.01); *A61B 2562/0233* (2013.01); *H04N 25/00* (2023.01)

(56) References Cited

U.S. PATENT DOCUMENTS

2009/0326321 A1* 12/2009 Jacobsen ............. A61B 5/6851
                                                                                                   600/109

2014/0143996 A1* 5/2014 Bhagavatula ........ G02B 6/3885
                                                                                                   29/428
2016/0219228 A1* 7/2016 Kintz .................... G02B 13/14
2018/0217364 A1     8/2018 Cocker et al.

FOREIGN PATENT DOCUMENTS

| WO | 2012027586 A2 | 3/2012 |
| WO | 2014071390 A1 | 5/2014 |
| WO | 2017079688 A1 | 5/2017 |

OTHER PUBLICATIONS

Murari et al.; "Design and characterization of a miniaturized epi-illuminated microscope"; Proceedings of the 31st Annual International Conference of the IEEE Engineering in Medicine and Biology Society; Sep. 3, 2009, pp. 5369-5372.
Smith et al.; "Cell-Phone-Based Platform for Biomedical Device Development and Education Applications"; PLOS One, vol. 6, No. 3, Mar. 2, 2011, p. e17150.
Flusberg et al.; "High-speed, miniaturized fluorescence microscopy in freely moving mice"; Nature Methods, vol. 6, No. 11, Oct. 5, 2008, pp. 935-938.
Ghosh et al.; "Miniaturized integration of a fluorescence microscope"; Nat. Methods, vol. 8, No. 10, Oct. 28, 2013, pp. 871-878.
Matthias et al.; "CMOS Image Sensor Wafer-level Packaging"; 2011 International Conference on Electronic Packaging Technology and High Density Packaging, 2011, pp. 1-6.

* cited by examiner

IMAGE-CAPTURING DEVICE, SYSTEM AND METHOD FOR CAPTURING IMAGES

The invention relates to an image-capturing device for the miniaturized near-field image capture of living biological tissue, in particular for the imaging of genetic indicators, wherein the image-capturing device comprises at least one digital image sensor and an objective lens in the form of a rod-shaped gradient index lens (GRIN), said objective lens being coupled to the digital image sensor for image capture. The invention additionally relates to a system for the miniaturized near-field image capture of a biological tissue, comprising such an image-capturing device and an evaluation device connected to the image-capturing device, and also a method for the miniaturized near-field image capture of biological tissue.

The invention generally relates to the field of capturing images of living biological tissue, e.g. of animals or humans. Such image-capturing devices, which are also referred to as fluorescence microscope or fluorescence endoscope, are used for example for the imaging of genetic activity markers in freely moving mice and other rodents. In contrast to the use of electrodes, the genetic specificity of the markers enabled individually defined cell populations to be imaged. This technique can therefore be described as complementary to traditional optogenetics: the cells are not or not only optically stimulated, but also optically read. If both techniques are combined with one another, this relates to the research field of so-called "Circuit Neuroscience".

An image-capturing device of the generic type is known from US 2018/0217364 A1, for example. The device therein is a relatively large structure, which limits the possibilities for use. Moreover, a multipartite construction with at least one baseplate is present, which requires specific handling of the device.

The invention is based on the object of specifying an improved image-capturing device by comparison thereof, a system and a method for capturing images.

In the case of an image-capturing device of the type mentioned in the introduction, this object is achieved by virtue of the fact that the objective lens is connected to the digital image sensor to form a monolithic, fixed structural unit, wherein between the objective lens and the digital image sensor there is no mechanical separating interface by way of which the digital image sensor is able to be separated from the objective lens by the user. Such an image-capturing device affords a large number of advantages. In this regard, such an image-capturing device is better able to be miniaturized because as a result of the monolithic construction in the form of a fixed structural unit it is precisely the case that particularly small individual components can be well combined with and connected to one another. A further advantage of the invention is that the monolithic, fixed structural unit does not have a mechanical separating interface between the objective lens and the digital image sensor, with the result that there is always a fixed connection between these components. Accordingly, focusing problems do not occur. If e.g. as in the prior art the objective lens and the digital image sensor are fitted together again, the image-capturing device in that case has to be manually refocused. This is obviated in the case of the image-capturing device according to the invention.

In addition, in this way the monolithic, fixed structural unit according to the invention is totally protected against ingress of dust, i.e. contamination effects of the optical system that occur in the prior art can be avoided. The fixed connection of the optical system additionally improves the image stability in moving animals and avoids other faults in the optical connection.

In addition, a structural unit formed from such components can be provided significantly more cost-effectively, such that it can also be embodied as a disposable product, i.e. as a throwaway article. As a result of the particularly greatly miniaturized design of the image-capturing device, moreover, the weight can be significantly reduced by comparison with known devices. In particular, a reduction of volume and weight by more than a factor of 300 is possible.

The image-capturing device can also be embodied completely without a mechanical separating interface of the elements belonging to the image-capturing device, i.e. all elements of the image-capturing device are part of the indivisible monolithic fixed structural unit.

The image-capturing device can be embodied without a dedicated housing. Accordingly, only the components required for forming the image-capturing device, i.e. at least the objective lens and the digital image sensor, are connected to one another via their housings or other mechanical elements. The image-capturing device can be embodied in particular without a separate supporting structure for stabilizing the individual components.

In accordance with one advantageous embodiment of the invention, it is provided that the image-capturing device comprises an electrical plug connector as sole connecting and separating interface of the image-capturing device that is operable by the user, by means of which plug connector the image-capturing device is connectable to an external power supply and/or evaluation unit via a line. The electrical plug connector can be connected to the digital image sensor directly or via a short cable. In this way, operability is simplified for the user and incorrect operations are largely avoided. In addition, the image-capturing device thus has no loose elements, or loose elements only to a very small extent. The digital image sensor can be connected mechanically directly to the electrical plug connector.

In accordance with one advantageous embodiment of the invention, it is provided that the digital image sensor is embodied as a wafer-level-packaged image sensor. This allows extremely great miniaturization of the image-capturing device. Such an image sensor is able to be realized with dimensions in the millimeter range. Such an image sensor can be produced for example with an integrated optical system, e.g. with a dedicated lens, directly on a silicone wafer. In this way, such an image sensor can progress far below the size and price limits of normal optoelectronics. By way of example, the image sensor can have a size of approximately 1.5×1.5×2 mm.

In accordance with one advantageous embodiment of the invention, it is provided that manual focusing by a user is not possible between the objective lens and the digital image sensor. In this way, the focusing effected during production is permanently maintained. Incorrect settings by the user can be avoided. In this way, the image capture quality can be significantly improved.

In accordance with one advantageous embodiment of the invention, it is provided that a spacer structurally integrated into the monolithic construction of the image-capturing device is arranged between the objective lens and the digital image sensor. By means of the spacer, the distance between the biological tissue to be captured and the electrical components of the image-capturing device can be increased and brought to a desired dimension. This makes it possible, despite the miniaturization of the image-capturing device, for the electrical components to be spaced at a sufficient distance from the biological tissue and for undesired changing effects to be avoided. The spacer can additionally provide the focusing between the objective lens and the digital image sensor.

In accordance with one advantageous embodiment of the invention, it is provided that a beam splitter structurally integrated into the monolithic construction of the image-capturing device is arranged between the objective lens and the digital image sensor. Such a beam splitter can create different light paths that can be used to realize additional functions on the image-capturing device, such as e.g. integrated illumination. The beam splitter can be embodied as a chroic beam splitter, i.e. as a beam splitter that differentiates between specific light colors or wavelengths of the light. The beam splitter can be embodied in particular as a dichroic or multichroic beam splitter. The spacer can then be arranged e.g. between the objective lens and the beam splitter.

In accordance with one advantageous embodiment of the invention, it is provided that the image-capturing device comprises a light source, in particular a fluorescence light source, which is configured for emitting light to the beam splitter, wherein the light source is structurally integrated in the monolithic construction of the image-capturing device. The light source can be used for various purposes, for example for the illumination of the region to be captured. Advantageously, the light source can be used in particular for the optical stimulation of genetically manipulated cells. By means of the beam splitter, the light from the light source can be coupled into the light path leading from the objective lens to the image sensor. The light source can be mounted on a backplate. The backplate serves for orientation of the light source and for cooling.

By virtue of the fact that the abovementioned components, in particular the spacer, the beam splitter and/or the light source, are structurally integrated into the monolithic construction of the image-capturing device, they are thus part of the integral fixed structural unit. The abovementioned components can thus also contribute to the mechanical stabilization and support of the entire construction of the image-capturing device. The digital image sensor can be coupled directly to an optical module of the image-capturing device having the beam splitter, the light source, optionally with a backplate, and the objective lens. As necessary, the spacer can additionally be part of the optical module.

Between the light source and the beam splitter there can be arranged a collimator, for example in the form of a lens, which converts the light emitted in a punctiform fashion by the light source, for example, into a parallel beam path that impinges on the beam splitter. In this way, the light from the light source can be emitted onto the biological tissue. Corresponding light reflected from the biological tissue is acquired by the objective lens and passes through the beam splitter vertically in the direction of the digital image sensor, where it can be recorded.

In accordance with one advantageous embodiment of the invention, it is provided that no real intermediate image of the image acquired by the objective lens is generated in the beam path between the objective lens and an image-capturing surface of the digital image sensor. In this case, the objective lens can be configured to focus the image acquired by the objective lens to infinity in the direction of the digital image sensor.

In accordance with one advantageous embodiment of the invention, it is provided that the components of the image-capturing device that are connected to one another to form a monolithic, fixed structural unit are connected to one another by means of adhesive and/or by means of frictionally locking connection. The adhesive can be an adhesive substance, e.g. quick-setting adhesive. The frictionally locking connection can be a clamping connection, for example. Further possibilities for connecting the components of the image-capturing device are positively locking coupling elements, such as e.g. a thread or a bayonet connection.

In accordance with one advantageous embodiment of the invention, it is provided that the image-capturing device is embodied as a disposable product. This has the advantage that a complicated construction with individual changeable components can be avoided and the application of the image-capturing device can thereby be simplified and made more reliable.

Stray light in the beam path of the image-capturing device can be suppressed by stops, for example. A stop can also be contained in the spacer, for example. Stray light can additionally be suppressed by an absorbent coating, or be reduced by pigments contained in the adhesive substance.

The beam path in the image-capturing device according to the invention can correspond to an epifluorescence microscope, for example, wherein in the case of the image-capturing device according to the invention no real intermediate image is generated between the objective lens and the digital image sensor. The excitation light supplied by the light source can be projected into a plane that is slightly offset with respect to the imaging plane. The emission light re-emitted by the biological tissue is focused approximately to infinity by the objective lens and is imaged through a lens of the digital image sensor onto the image-capturing surface thereof.

The digital image sensor can be embodied like a miniature camera. For this purpose, the digital image sensor can also comprise an integrated lens besides the actual sensor element.

The excitation light from the light source can be subjected to bandpass filtering in the optical module; the emission light emitted by the biological tissue can likewise be subjected to either bandpass filtering or long-pass filtering.

The beam splitter can be embodied with a splitting wavelength that is approximately midway between the excitation light and the emission light. Stray light stops can be situated in the beam path, e.g. at the transition from the light source to the beam splitter, for example at the tube, and/or directly upstream of the digital image sensor and/or upstream of the objective lens.

The image-capturing device, depending on the embodiment, can be realized with a dedicated electrical energy source and/or a storage unit for the captured images. Alternatively or additionally, data and/or electrical energy can be transmitted via a cable via which the image-capturing device is connected to an evaluation device. The cable can be connected to the plug connector of the image-capturing device by means of an electrical plug. The cable can have a rotary load relieving means, e.g. a slip ring, and is connected to the evaluation device. The evaluation device can be embodied for acquiring the transmitted data and for displaying the data.

The use of a wafer-level-packaged image sensor results in enormous advantages in terms of size and weight. In this regard, at least the actual sensor and the electrical circuit that controls the sensor can be connected to one another directly at the chip level and form one unit. In this way, only a few lines are needed for data transfer. The digital image sensor can be embodied as a camera and, in this case, contain a lens directly. An additional diffracting element (lens, stop, diffractive element) can also be installed in the image-capturing device between the image sensor and the optical module, in particular the objective lens. A microcomputer system may already have been integrated in the image-capturing device, which system automatically analyzes the captured data of the image sensor, e.g. with regard to cell extraction or detection of brightness transients. In this way, it is possible to reduce the required bandwidth for the data transfer from the image-capturing device to the evaluation device.

The image-capturing device can be realized in a form that is expedient for securing on a test animal, e.g. by means of adhesive or by friction. For this purpose, the outer surface of the image-capturing device can either be rough or uneven, or it can have projections around which an adhesive substance can flow.

If the image-capturing device is realized without a dedicated housing, it can be protected against external light influences by coating with a light-absorbing composition. The light-absorbing composition can be sprayed for example onto the exterior of the image-capturing device, or be applied thereto in some other way. In this way, a complete enclosing body of the image-capturing device is not necessary.

The light source can be a semiconductor light source, e.g. an LED, a laser diode or a VCSEL laser. The light source can be configured in particular for at least approximately parallel emission of the light, e.g. by virtue of the light source comprising a parabolic mirror or a lens. The collimator can be embodied as a lens, a GRIN element or a diffractive element, or as a combination of such elements.

The light source can likewise be connected to the electrical plug connector of the image-capturing device in order to be supplied with electrical energy. This electrical connection can be realized for example by a thin cable, e.g. a polyimide flexible cable, or in the form of an electrically conductive coating. The electrically conductive coating can be realized e.g. by a spatial printing process, e.g. aerosol direct writing. It is also possible for a metallization to be applied on the outer surface by vapor deposition.

The excitation and emission filters used can be interference filters and/or absorbent color filters. These filters can be applied directly on optical surfaces of the image-capturing device or be dissolved in the body of optical elements, e.g. lenses as colorant.

The beam splitter can be formed from glass or plastic, e.g. from a polymer. It can have the shape of a cube or parallelepiped, for example. The layer that brings about the optical filtering can be applied by vapor deposition or spraying, for example. The filter layer can also be realized as thin film, e.g. as a film having a layer thickness of less than 200 μm.

The parts of the image-capturing device, in particular the optically effective components, can be produced by plastic injection-molding methods and/or by 3D printing methods.

The objective lens can also image the object plane directly into the plane of the image-capturing surface of the digital image sensor. The objective lens has a capturing side, at which the light from the light source can be emitted and light received on this side can be fed to the digital image sensor. At the capturing side the objective lens can have a light deflecting apparatus, e.g. a microprism or a grating is secured, which allows the imaging toward the side, i.e. at a specific angle with respect to the longitudinal axis of the objective lens.

The evaluation device can have software for analyzing the data.

The invention additionally relates to a system for the miniaturized near-field image capture of biological tissue, comprising an image-capturing device of the type explained above and an evaluation device connected to the image-capturing device. The advantages explained above can be realized by this means, too.

The invention additionally relates to a method for the miniaturized near-field image capture of a biological tissue, in particular for the imaging of genetic indicators in the biological tissue, wherein the image capture is carried out by means of an image-capturing device of the type explained above. The advantages explained above can be realized by this means, too.

The invention can use genetic activity markers that can be detected in the brain of mammals or humans in order to draw corresponding conclusions about the processes within the cells expressing them. By way of example, it is possible to measure the increase in the fluorescence of genetic calcium indicators that occurs in the event of neural activity in neurons as a result of calcium being released, and it is thereby possible to detect the neural activity. For this purpose, the image-capturing device continuously acquires images of the tissue which is situated directly beneath the objective lens and is illuminated by the integrated light source.

The activity markers or the corresponding genetic information are/is either already contained in the animal—if a corresponding transgenic animal line is involved—or are/is introduced into the cells be examined by a genetic engineering method (e.g. viral vector, electroporation). For this purpose, and in particular for subsequent implantation, the skull is opened up. The objective lens is then implanted in the tissue such that it covers the transgenic region, that is to say can image the markers in the cells of interest. Afterward, the still exposed brain is protected by a protective layer composed of silicone, for example, and the still exposed part of the implant is connected—by a cement, for example—fixedly to the skull or a structure that is routed, relative to the examined tissue, in order to avoid blurring of the images. Subsequently, under certain circumstances, more extensive wound closure is also effected. In the case where the cells first have to produce the genetic marker after implantation, there follows a waiting period until the marker is present in a sufficient concentration. A waiting time of approximately 2-4 weeks is typically necessary anyway, however, until the tissue in front of the lens has recovered from the intervention and activity at the individual cell level becomes visible.

The image-capturing device subsequently acquires the region of interest either in the context of a specific neurobiological experiment or during normal behavior. Image refresh rates of 1-100 Hz, usually 5-30 Hz, are advantageous. The acquisition duration is typically minutes to hours but, depending on the issue being investigated, the acquisition can also be continuous—for example as a brain-machine interface in order to continuously read out brain activity from the brain of paralyzed patients. If the acquisition is not effected continuously, the image-capturing device is disconnected at the plug connector so that the connecting cable does not further restrict the subject. The connecting cable is corresponding reattached for the next experiment.

The image-capturing device can comprise one or more further sensors, e.g. at least one calcium sensor and/or at least one voltage sensor. Such sensors can be used to capture the neural activity in neurons.

The invention is explained in greater detail below on the basis of exemplary embodiments using drawings.

Figure 1:
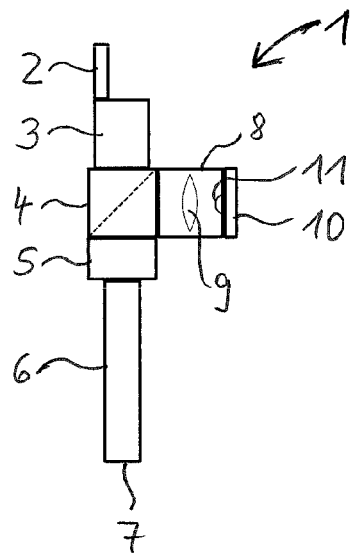
FIG. 1 shows an image-capturing device in side view.

The image-capturing device 1 in accordance with FIG. 1 comprises a digital image sensor 3, which can be embodied as a wafer-level-packaged image sensor. An electrical plug connector 2, e.g. in the form of a socket, is arranged at the image sensor 3. At its side configured for image capture, the image sensor 3 is coupled to a beam splitter 4. The beam splitter 4 can be embodied as a chroic beam splitter, i.e. as a beam splitter that differentiates between specific light colors or wavelengths of the light.

A light source 11 is additionally fitted to the beam splitter 4. The light source 11 is mounted on a backplate 10. The arrangement of the backplate 10 with the light source 11 is connected to the beam splitter 4 via a lens mount 8. There can be arranged in the lens mount 8 a lens 9, e.g. a collimation lens, which converts light emitted in a substantially punctiform fashion by the light source 11 into a substantially parallel beam path.

An objective lens 6 is arranged in the further beam path from the image sensor 3 toward an image acquisition region 7 of the image-capturing device 1, said objective lens being coupled to the beam splitter 4 via a spacer 5. The objective lens 6 is embodied as a rod-shaped gradient index lens.

In the case of the described construction of the image-capturing device 1, the objective lens 6, the spacer 5 (which is optional), the light source 11 with the backplate 10 and the lens mount 8 can be coupled to the beam splitter 4 to form a monolithic optical module. Said optical module is connected to the digital image sensor 3 to form a monolithic fixed structural unit.

Figure 2:
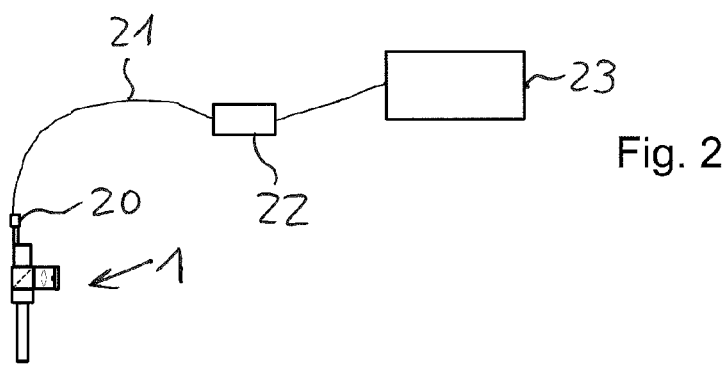
FIG. 2 shows a system for capturing images.

FIG. 2 shows a system for capturing images, comprising an image-capturing device 1 and an evaluation device 23. The evaluation device 23 is coupled to the image-capturing device 1 via a cable 21. For this purpose, at its end the cable 21 has a plug 20, which is coupled to the electrical plug connector 2 of the image-capturing device 1. In addition, the cable 21 can have a rotary load relieving means 22 in order to minimize torsional loads of the cable 21. By means of the image-capturing device 1, images can be captured by way of the image acquisition region 7 and be transmitted to the evaluation device 23 via the cable 21. The captured images can be evaluated in the evaluation device 23. In addition, the evaluation device 23 can be configured for controlling the image-capturing device, e.g. for driving the light source 11, and can emit corresponding control signals to the image-capturing device 1.

Figure 3:
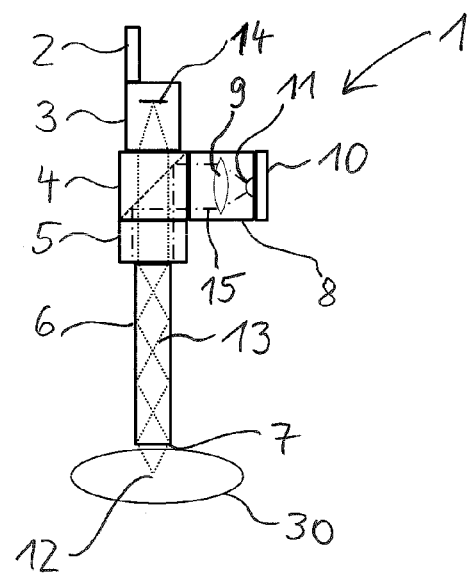
FIG. 3 shows the image-capturing device in accordance with FIG. 1 with further details.

FIG. 3 shows the image-capturing device 1 with light beam paths depicted therein. In the case of the digital image sensor 3, the image-capturing surface 14 thereof is additionally depicted.

Light emitted by the light source 11 is converted into a substantially parallel beam path 15 by means of the lens 9. The beam path 15 is deflected in the direction of the objective lens 6 by means of the beam splitter 4 and is emitted by the objective lens 6 in the image acquisition region 7. The emitted light impinges on biological tissue 30. Light emitted from there in turn is acquired at a location 12 onto which the objective lens 6 focuses, and is forwarded via the objective lens 6 by means of the depicted beam path 13 running crosswise. The objective lens 6 focuses to infinity in the direction of the digital image sensor 3, that is to say that a substantially parallel beam path is forwarded via the spacer 5 and the beam splitter 4. Via a lens integrated in the digital image sensor 3, the incoming parallel beam path is focused onto the image-capturing surface 14.

The invention claimed is:

1. An epifluorescence image-capturing device for a miniaturized near-field image capture of biological tissue and/or imaging of genetic indicators, comprising:
   at least one digital image sensor in the form of a wafer-level-packaged image sensor comprising an image-capturing surface and an integrated optical system directly on the wafer;
   an objective lens in a form of a rod-shaped gradient index lens (GRIN), said objective lens being coupled to the at least one digital image sensor for image capture, said objective lens being configured to focus an image to infinity in a direction of the at least one digital image sensor; and
   a dichroic or multichroic beam splitter structurally arranged between the objective lens and the at least one digital image sensor, wherein the dichroic or multichroic beamsplitter is formed from glass or plastic, wherein the dichroic or multichroic beam splitter is configured to couple light for illuminating a region to be captured into a light path leading from the objective lens to the at least one digital image sensor,
   wherein the light path leading from the objective lens reaches and passes through the dichroic or multichroic beam splitter to reach the at least one digital image sensor,
   wherein the dichroic or multichroic beam splitter is configured to differentiate between specific light colors,
   wherein the objective lens, the dichroic or multichroic beam splitter, and the at least one digital image sensor are connected together to form a monolithic, fixed structural unit,
   wherein the integrated optical system of the at least one digital image sensor is configured to focus the image from the objective lens onto the image-capturing surface of the at least one digital image sensor,
   wherein between the objective lens and the at least one digital image sensor there is no mechanical separating interface by way of which the at least one digital image sensor is able to be separated from the objective lens by a user,
   wherein manual focusing by the user is not possible between the objective lens and the at least one digital image sensor.

2. The epifluorescence image-capturing device as claimed in claim 1, further comprising an electrical plug connector as a sole connecting and separating interface that is operable by the user, wherein the electrical plug connector is connectable to an external power supply and/or evaluation unit via a line.

3. The epifluorescence image-capturing device as claimed in claim 1 further comprising a spacer structurally integrated into the monolithic, fixed structural unit of the epifluorescence image-capturing device, wherein the spacer is arranged between the objective lens and the dichroic or multichroic beam splitter, wherein the spacer is configured for providing a fixed distance between the objective lens and the at least one digital image sensor, wherein the spacer is not configured to focus, disperse, or collimate light.

4. The epifluorescence image-capturing device as claimed in claim 1 further comprising a light source configured for emitting light to the dichroic or multichroic beam splitter, wherein the light source is structurally integrated in the monolithic, fixed structural unit of the epifluorescence image-capturing device.

5. The epifluorescence image-capturing device as claimed in claim 4 wherein the light source is a fluorescent light source.

6. The epifluorescence image-capturing device as claimed in claim 1 wherein no real intermediate image of an image acquired by the objective lens is generated in a beam path between the objective lens and an image-capturing surface of the at least one digital image sensor.

7. The epifluorescence image-capturing device as claimed in claim 1 wherein components of the epifluorescence image-capturing device that are connected to one another to form the monolithic, fixed structural unit are connected to one another by adhesive and/or by frictionally locking connection.

8. The epifluorescence image-capturing device as claimed in claim 1 wherein the epifluorescence image-capturing device is embodied as a disposable product.

9. A system for a miniaturized near-field image capture of biological tissue, comprising:
   the epifluorescence image-capturing device as claimed in claim 1; and
   an evaluation device connected to the epifluorescence image-capturing device.

* * * * *